United States Patent [19]

Elbe et al.

[11] Patent Number: 5,356,899

[45] Date of Patent: Oct. 18, 1994

[54] SUBSTITUTED HYDROXYALKYLPYRIDINES

[75] Inventors: Hans-Ludwig Elbe, Wuppertal; Stefan Böhm, Cologne; Ralf Tiemann, Leverkusen; Stefan Dutzmann, Hilden; Heinz-Wilhelm Dehne, Monheim, all of Fed. Rep. of Germany

[73] Assignee: Bayer Aktiengesellschaft, Leverkusen, Fed. Rep. of Germany

[21] Appl. No.: 113,482

[22] Filed: Aug. 27, 1993

[30] Foreign Application Priority Data

Sep. 4, 1992 [DE] Fed. Rep. of Germany ....... 4229643

[51] Int. Cl.$^5$ ............................................. A01N 43/40
[52] U.S. Cl. .................................... 514/277; 546/343; 546/344
[58] Field of Search ................. 546/344, 343; 514/277

[56] References Cited

U.S. PATENT DOCUMENTS

| | | | |
|---|---|---|---|
| 4,518,600 | 5/1985 | Holmwood et al. | 514/256 |
| 4,677,128 | 6/1987 | Place et al. | 514/277 |
| 5,047,544 | 9/1991 | Elbe et al. | 514/277 |
| 5,174,997 | 12/1992 | Zierke et al. | 424/405 |

FOREIGN PATENT DOCUMENTS

| | | |
|---|---|---|
| 0221844 | 10/1986 | European Pat. Off. . |
| 0302366 | 2/1989 | European Pat. Off. . |
| 441207 | 1/1991 | European Pat. Off. . |
| 2742173 | 3/1979 | Fed. Rep. of Germany . |
| 3150138 | 6/1983 | Fed. Rep. of Germany . |
| 3435545 | 5/1986 | Fed. Rep. of Germany . |
| 620910 | 12/1980 | Switzerland . |

OTHER PUBLICATIONS

Monatshefte fur Chemie 122, 871–(1991).
Monatshefte fur Chemie 122, 879–885 (1991).

*Primary Examiner*—C. Warren Ivy
*Assistant Examiner*—A. A. Owens
*Attorney, Agent, or Firm*—Sprung Horn Kramer & Woods

[57] ABSTRACT

Novel substituted hydroxyalkylpyridines of the formula (I),

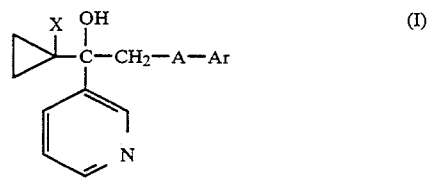

in which x, A and Ar have the meanings given in the description and their acid addition salts and metal salt complexes and their use for combating pests, in particular in the field of plant protection and in the protection of materials.

The compounds of the formula (I) may be prepared according to known processes, for example from suitable cyclopropyl ketones and organometallic pyridine compounds.

12 Claims, No Drawings

SUBSTITUTED HYDROXYALKYLPYRIDINES

The invention relates to novel substituted hydroxyalkylpyridines, a process for their preparation and their use in agents for combating pests.

It is known that certain substituted hydroxyalkylpyridines, such as, for example, the compound 4-(4-chlorophenoxy)-2,2-dimethyl-3-hydroxy-1-phenyl-3-(3-pyridyl)-butane, possess fungicidal properties (cf. e.g. EP 302 366).

However, the activity of these previously known compounds, in particular when using low amounts and concentrations, is not completely satisfactory in all areas of application.

Novel substituted hydroxyalkylpyridines of the formula (I),

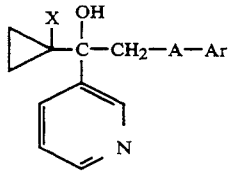

in which
X represents halogen,
A represents oxygen or sulphur and
Ar represents optionally substituted aryl, and their acid addition salts and metal salt complexes have been found.

The compounds of the formula (I) contain at least one asymmetrically substituted carbon atom and can therefor exist as optical isomers or isomeric mixtures of varying composition. Both the pure isomers and the isomeric mixtures are claimed according to the invention. Additionally, it has been found that the novel substituted hydroxyalkylpyridines of the formula (I)

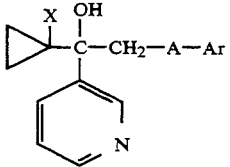

in which
X represents halogen,
A represents oxygen or sulphur and
Ar represents optionally substituted aryl,
and their acid addition salts and metal salt complexes are obtained if cyclopropyl ketones of the formula (II),

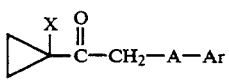

in which X, A and Ar have the abovementioned meanings, are reacted with organometallic pyridine compounds of the formula (III),

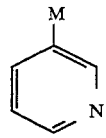

in which M represents a lithium atom or a magnesium-halogen grouping, optionally in the presence of a diluent and, if appropriate, an acid or a metal salt is added on to the resulting compounds of the formula (I).

Finally, it has been found that the novel substituted hydroxyalkylpyridines of the formula (I) posses good activity against pests.

Surprisingly, the substituted hydroxyalkylpyridines of the formula (I) according to the invention show substantially superior activity against plant-damaging microorganisms in comparison with the substituted hydroxyalkylpyridines known from the prior art, such as, for example, the compound 4-(4-chlorophenoxy)-2,2-dimethyl-3-hydroxy-1-phenyl-3-(3-pyridyl)-butane, which are closely related compounds with regard to their chemistry and/or their action.

The substituted hydroxyalkylpyridines according to the invention are defined generally by the formula (I). Compounds of the formula (I) are preferred in which
X represents fluorine, chlorine, bromine or iodine,
A represents oxygen or sulphur and
Ar represents aryl having 6 to 10 carbon atoms, which is optionally substituted identically or differently once or more than once, with suitable substituents in each case being:
halogen, cyano, nitro, in each case straight-chain or branched alkyl, alkoxy, alkylthio, alkylsulphinyl or alkylsulphonyl having in each case 1 to 4 carbon atoms, in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, in each case straight-chain or branched alkoxycarbonyl or alkoximinoalkyl having in each case 1 to 4 carbon atoms in the individual alkyl moieties, cycloalkyl having 3 to 8 carbon atoms as well as phenyl, which is optionally substituted identically or differently once to more than once by halogen, straight-chain or branched alkyl, straight-chain or branched alkoxy, straight-chain or branched halogenoalkyl and/or straight-chain or branched halogenoalkoxy having in each case 1 to 4 carbon atoms and optionally 1 to 9 identical or different halogen atoms.

Compounds of the formula (I) are particularly preferred in which
X represents fluorine, chlorine or bromine,
A represents oxygen or sulphur and
Ar represents aryl having 6 or 10 carbon atoms, e.g. phenyl and naphthyl, which is optionally substituted identically or differently once to five times, with suitable substituents in each case being:
halogen, cyano, nitro, in each case straight-chain or branched alkyl, alkoxy, alkylthio, alkylsulphinyl or alkylsulphonyl having in each case 1 to 3 carbon atoms, in each case straight-chain or branched halogenoalkyl, halogenoalkoxy, halogenoalkylthio, halogenoalkylsulphinyl or halogenoalkylsulphonyl having in each case 1 to 3 carbon atoms and 1 to 7 identical or different halogen atoms, in each case straight-chain or branched alkoxycarbonyl or alkoxyiminoalkyl having in each case 1 to 3 carbon atoms in the individual alkyl moieties, cycloalkyl having 3 to 7 carbon atoms as well as phenyl, which is optionally substituted identically or differently once to five times by halogen, straight-chain or branched alkyl, straight-chain or branched alkoxy, straight-chain or branched halogenoalkyl and/or straight-chain or branched halogenoalkoxy having in each case 1 to 3 carbon atoms and optionally 1 to 7 identical or different halogen atoms.

Compounds of the formula (I) are very particularly preferred in which

X represents fluorine or chlorine,

A represents oxygen or sulphur and

Ar represents phenyl, which is optionally substituted identically or differently once to five times, with suitable substituents in each case being:

fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, methylsulphinyl, ethylsulphinyl, methylsulphonyl, ethylsulphonyl, trifluoromethyl, difluoromethyl, trifluoromethoxy, difluoromethoxy, trifluoromethylthio, trifluoromethylsulphinyl, trifluoromethylsulphonyl, methoxycarbonyl, ethoxycarbonyl, methoxyiminomethyl, methoxyiminoethyl, ethoxyiminomethyl, ethoxyiminoethyl, cyclopropyl, cyclopentyl, cyclohexyl or phenyl, which is optionally substituted identically or differently once to three times by fluorine, chlorine, bromine, methyl, ethyl, n- or i-propyl, methoxy, ethoxy, trifluoromethyl and/or trifluoromethoxy.

Other preferred substances according to the invention are addition products of acids and those substituted hydroxyalkylpyridines of the formula (I) in which X, A and Ar have the meanings mentioned above as being preferred.

The acids which can be added on preferably include hydrohalic acids such as, for example, hydrochloric acid and hydrobromic acid, in particular hydrochloric acid, furthermore phosphoric acid, nitric acid, sulphuric acid, mono- and bifunctional carboxylic acids and hydroxycarboxylic acids such as, for example, acetic acid, maleic acid, succinic acid, fumaric acid, tartaric acid, citric acid, salicylic acid, sorbic acid and lactic acid, as well as sulphonic acids such as, for example, p-toluenesulphonic acid, 1,5-naphthalenedisulphonic acid or camphorsulphonic acid, and furthermore also saccharine and thiosaccharine.

Other preferred substances according to the invention are addition products of salts of metals of main group II to IV and sub-group I and II as well as IV to VIII of the Periodic System of the Elements and substituted hydroxyalkylpyridines of the formula (I) in which X, A and Ar have the meanings mentioned above as being preferred.

Salts of copper, zinc, manganese, magnesium, tin, iron and of nickel are particularly preferred in this context. Suitable anions of these salts are those which are derived from those acids which give physiologically acceptable addition products. Acids of this type which are particularly preferred in this context are the hydrohalic acids such as, for example, hydrochloric acid and hydrobromic acid, furthermore phosphoric acid, nitric acid and sulphuric acid.

If, for example, 1-chlorocyclopropyl-2-(2,4-dichlorophenoxy)-ethan-1-one and 3-pyridyl-lithium are used as starting compounds, the course of the reaction of the process according to the invention may be represented by the following formula diagram:

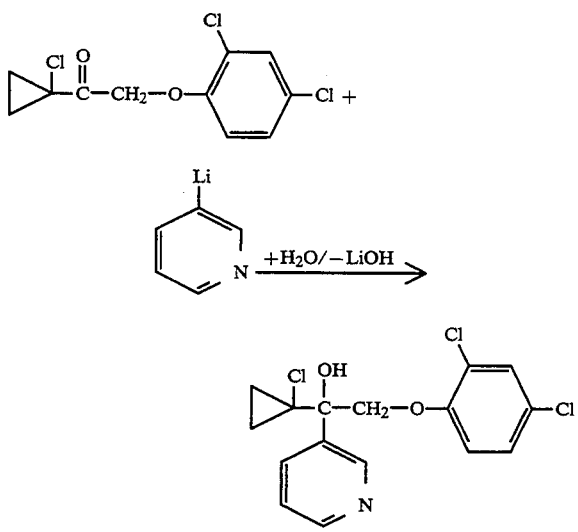

The cyclopropyl ketones which are required as starting materials for carrying out the process according to the invention are generally defined by the formula (II). In this formula (II), X, A and Ar preferably represent those radicals which have already been mentioned, in connection with the description of the compounds of the formula (I) according to the invention, as being preferred for these substituents.

The cyclopropyl ketones of the formula (II) are known or can be obtained in analogy to known processes (cf. e.g. EP 297 383).

The organometallic pyridine compounds which are additionally required as starting materials for carrying out the process according to the invention are generally defined by the formula (III). In this formula (III), M preferably represents a lithium atom or a Mg-Cl radical or a Mg-Br radical.

The organometallic pyridine compounds of the formula (III) are well-known compounds in organic chemistry.

Inert organic solvents are suitable diluents for carrying out the process according to the invention. Among these are, in particular, aliphatic, alicyclic or aromatic hydrocarbons, such as, for example, benzine, benzene, toluene, xylene, petroleum ether, hexane, cyclohexane or ethers, such as diethyl ether, diisopropyl ether, dioxane, tetrahydrofuran or ethylene glycol dimethyl ether or ethylene glycol diethyl ether or amides, such as hexamethylphosphoric triamide.

In carrying out the process according to the invention, the reaction temperatures may be varied over a relatively wide range. In general, temperatures of between −100° C. and +150° C., preferably temperatures of between −80° C. and +120° C., are employed.

The process according to the invention is customarily carried out under atmospheric pressure. However, it is also possible to carry it out under elevated or reduced pressure.

For carrying out the process according to the invention, 1.0 to 3.0 mol, preferably 1.0 to 1.5 mol, of organometallic pyridine compound of the formula (III) is generally employed per mol of cyclopropyl ketone of the formula (II). The performance of the reaction, working up and isolation of the reaction products takes place according to customary methods. In the process, the reaction can, if required, be carried out in the presence of a suitable inert gas, such as, for example, nitrogen or helium. It is also possible to prepare the organometallic pyridine compound of the formula (III), which is to be employed as a reactant, from appropriate starting compounds such as, for example, 3-bromopyridine and isopropylmagnesium bromide or butyllithium directly in the reaction vessel in a preliminary reaction and, without isolation, subsequently to react it further in a one-pot process with the cyclopropyl ketones of the formula (II) according to the process according to the invention (cf. in this context the preparation examples as well).

The purification of the end products of the formula (I) is effected using customary procedures, for example by column chromatography or by recrystallisation.

The substituted hydroxyalkylpyridines of the formula (I) according to the invention can be converted into acid addition salts or metal salt complexes.

Suitable acids for the preparation of acid addition salts of the compounds of the formula (I) are preferably those which have already been mentioned in connection with the description of the acid addition salts according to the invention as being preferred.

The acid addition salts of the compounds of the formula (I) can be obtained in a simple manner by customary salt formation methods, for example by dissolving a compound of the formula (I) in a suitable inert solvent and adding the acid, for example hydrochloric acid, and isolated in a customary manner, for example by filtration, and, if appropriate, purified by washing with an inert organic solvent.

Suitable salts for the preparation of metal salt complexes of the compounds of the formula (I) are preferably those salts of metals which have already been mentioned in connection with the description of the metal salt complexes according to the invention as being preferred metal salts.

The metal salt complexes of the compounds of the formula (I) can be obtained in a simple manner by customary processes, for example by dissolving the metal salt in alcohol, for example ethanol, and adding the solution to compounds of the formula (I). Metal salt complexes can be isolated in a known manner, for example by filtration, and, if appropriate, purified by recrystallisation.

Characterisation takes place using the melting point or, in the case of non-crystallising compounds, using the refractive index or proton nuclear magnetic resonance spectroscopy ($^1$H-NMR).

The active compounds according to the invention exhibit a strong effect against pests and can be employed in practice for combating unwanted pernicious organisms. The active compounds are suitable for use as plant protective agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *Peronospora brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *Pyrenophora graminea* (conidia form: Drechslera, synonym: Helminthosporium);

Cochliobolus species, such as, for example, *Cochliobolus sativus* (conidia form: Drechslera, synonym: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae;* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this context, the active compounds according to the invention may be employed particularly successfully for combating cereal diseases, such as, for example, against the causative agent of net blotch in barley (*Pyrenophora teres*) or against the causative agent of spot blotch in barley or wheat (*Cochliobolus sativus*) or against the causative agent of glume blotch in wheat (*Leptosphaeria nodorum*) or against the causative agent of powdery mildew in wheat or barley (*Erysiphe graminis*), or against the causative agent of stem break in cereals (*Pseudocercosporella herpotrichoides*), against Fusarium species or for combating diseases in fruit and vegetable cultivation, such as, for example, against the causative agent of grapevine powdery mildew (*Un-* cinula necator) or against the causative agent of apple scab (*Venturia inaequalis*) or against the causative agent of cucumber powdery mildew (*Sphaerotheca fuliginea*) or against the causative agent of apple mildew (*Podosphaera leucotricha*) or for combating rice diseases, such as, for example, against the causative agent of rice blast disease (*Pyricularia oryzae*) or against the causative agent of stem blight in rice (*Pellicularia sasakii*). In addition, the active compounds according to the invention also possess broad and effective in vitro activity.

Depending on their particular physical and/or chemical properties, the active compounds can be converted to the customary formulations, such as solutions, emulsions, suspensions, powders, foams, pastes, granules, aerosols, very fine encapsulations in polymeric substances and in enveloping compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide or dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilisers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range: they are, in general, between 1 and 0.0001% by weight, preferably between 0.5 and 0.001% by weight.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

Besides the above-noted activity against microorganisms which are pathogenic for plants, the active compounds according to the invention are marked by a broad and strong microbicidal effect against a broad spectrum of microorganisms which are relevant in relation to the protection of materials, as well as by conspicuously good activity against algae and slime organisms. The substances according to the invention are therefore particularly well suited for protecting industrial materials.

Industrial materials in this sense are inanimate materials which have been prepared for industrial use. For example, industrial materials which are to be protected from microbial change or destruction by active compounds according to the invention may be adhesives, glues, paper and cardboard, textiles, leather, wood, brush-on-coatings, and synthetic articles, coolant lubricants and other materials which may be attacked or decomposed by microorganisms. Parts of production plants, such as, for example, cooling-water circuits, which can be impaired by the multiplication of microorganisms, may also be mentioned within the scope of the materials to be protected. Industrial materials which may preferably be mentioned within the scope of the present invention are adhesives, glues, papers and cardboards, leather, wood, lacquers and paints, synthetic articles, coolant lubricants and coolant circuits.

Examples which may be mentioned of microorganisms which can bring about degradation or change of the industrial materials are bacteria, fungi, yeasts, algae and slime organisms. The active compounds according to the invention act preferably against fungi, in particular moulds, and against wood-discolouring and wooddestroying fungi (Basidiomycetes), as well as against slime organisms and algae.

Microorganisms of the following genera may be mentioned as examples:
Alternaria, such as *Alternaria tenuis*,
Aspergillus, such as *Aspergillus niger*;
Achaetomium, such as *Chaetomium globosum*;
Coniophora, such as *Coniophora puteana*;
Lentinus, such as *Lentinus tigrinus*;
Penicillium, such as *Penicillium glaucum*;
Polyporus, such as *Polyporus versicolor*;
Aureobasidium, such as *Aureobasidium pullulans*;
Sclerophoma, such as *Sclerophoma pityophila*;
Trichoderma, such as *Trichoderma viride*;
Escherichia, such as *Escherichia coli*;
Pseudomonas, such as *Pseudomonas aeruginosa*;
Staphylococcus, such as *Staphylococcus aureus*.

Depending on the field of application, an active compound according to the invention can be converted into the customary formulations, such as solutions, emulsions, suspensions, powders, pastes or granules.

These may be prepared in a manner known per se, for example by mixing the active compounds together with an extender, which is composed of a liquid solvent and/or solid carrier substances, optionally using surface-active agents, such as emulsifiers and/or dispersing agents, it being possible to use organic solvents such as alcohols as adjuvants when water is used as the extender. Liquid solvents for the active compounds may, for example, be water, alcohols, preferably ethanol or isopropanol or benzyl alcohol, ketones, such as acetone or methyl ethyl ketone, liquid hydrocarbons, such as benzine fractions, halogenated hydrocarbons, such as 1,2-dichloroethane.

Microbicidal agents generally contain the active compounds in a quantity of 1 to 95%, preferably of 10 to 75%.

The concentrations at which the active compounds according to the invention are used depend on the nature and the incidence of the microorganisms which are to be controlled, as well as on the composition of the material to be protected. The optimum quantity to be used can be elucidated by series of tests..In general, the concentrations to be used are in the range from 0.001 to 5% by weight, preferably from 0.05 to 1.0% by weight, based on the material to be protected.

The active compounds according to the invention may also be present in a mixture together with other known active compounds. The following active compounds may be mentioned as examples: benzyl alcohol mono(or poly)hemiformal and other formaldehyde-eliminating compounds, benzimidazolyl methylcarbamates, tetramethyldiuram disulphide, zinc salts of dialkyldithiocarbamates, 2,4,5,6-tetrachloroisophthalonitrile, thiazolylbenzimidazole, mercaptobenzothiazole, organo-tin compounds, methylenebisthiocyanate, phenol derivatives, such as 2-phenylphenol, (2,2'-dihydroxy-5,5'-dichloro)-diphenylmethane, 3-methyl-4-chlorophenol, 2-thiocyanatomethylthiobenzothiazole, N-trihalogenomethylthio compounds, such as folpet, fluorofolpet and dichlofluanid, azole fungicides, such as triadimefon, triadimenol, bitertanol, tebuconazole, propiconazole, azoconazole, iodopropargyl derivatives, such as iodopropargyl butylcarbamate and iodopropargyl phenylcarbamate, iodothiazolinone compounds, such as Kathon, as well as quaternary ammonium compounds, such as benzalkonium chloride.

Mixtures of the substances to be used according to the invention may likewise be employed together with known insecticides. By way of example, the following may be mentioned here: organophosphorus compounds, such as chlorpyriphos or phoxim, carbamates, such as aldicarb, carbosulfan or propoxur or pyrethroids, such as permethrin, cyfluthrin, cypermethrin, deltamethrin or fenvalerate.

Algicides, molluscicides and active substances against "sea animals", which settle on the coatings of ships' bottoms, are also suitable partners in mixtures.

PREPARATION EXAMPLES

Example 1

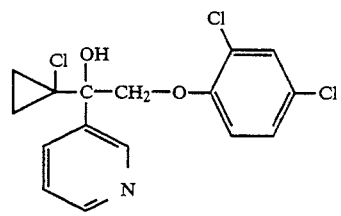

A solution of 30.6 g (0.1 mol) of n-butyllithium in n-hexane (23%) is added dropwise while stirring at −80° C. and under a dry nitrogen atmosphere to 15.8 g (0.1 mol) of 3-bromopyridine, which are dissolved in a mixture of 80 ml of diethyl ether and 80 ml of tetrahydrofuran. After the addition is complete, the mixture is stirred for a further 20 minutes at this temperature, and then a solution of 28.0 g (0.1 mol) of 1-chlorocyclopropyl-2-(2,4-dichlorophenoxy)-ethan-1-one in 100 ml of tetrahydrofuran is added, likewise at −80° C., and the mixture is subsequently stirred for a further 30 minutes at −80° C.; the reaction mixture is then allowed to come to room temperature within the course of 2 hours, 140 ml of saturated aqueous ammonium chloride solution are added, the organic phase is separated off, washed twice with water, and dried over sodium sulphate, and the solvent is removed in vacuo. The residue is purified by chromatography on silica gel (eluent: diethyl ether).

18.3 g (51% of theory) of 1-(1-chlorocyclopropyl)-1-(3-pyridyl)-2-(2,4-dichlorophenoxy)-ethanol are obtained as an oil.

$^1$H-NMR (CDCl$_3$/tetramethylsilane): δ=3.68 ppm (1H)

Preparation of the Starting Compound

Example II-1

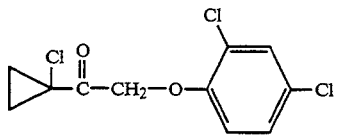

15.3 g (0.1 mol) of 1-chlorocyclopropyl-2-chloro-2-ethan-1-one (cf. e.g. EP 297 383), 18 g (0.11 mol) of 2,4-dichlorophenol and 16.5 g (0.12 mol) of potassium carbonate are heated at reflux temperature in 100 ml of toluene for 8 hours while stirring. For the working up, the cooled reaction mixture is added to water, the organic phase is separated off, washed three times with 10 per cent sodium hydroxide solution, dried over sodium sulphate and concentrated in vacuo, and the residue is directly subjected to further reaction without additional purification.

25.8 g (92% of theory) of 1-chlorocyclopropyl-2-(2,4-dichlorophenoxy)-ethan-1-one are obtained as an oil.

Example 2

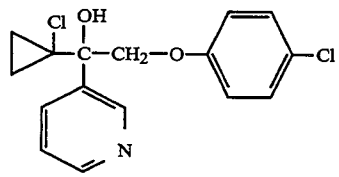

25.6 g (0.162 mol) of 3-bromopyridine—dissolved in 140 ml of tetrahydrofuran—are run, at room temperature while stirring, into a solution of 23.8 g (0.162 mol) of isopropylmagnesium bromide in 140 ml of diethyl ether. During this process, the temperature of the reaction mixture rises to the reflux temperature. After the addition is complete, the mixture is stirred at this temperature for a further 30 minutes, and then a solution of 33.0 g (0.135 mol) of 1-chlorocyclopropyl-2-(4-chlorophenoxy)-ethan-1-one in 100 ml of tetrahydrofuran is added dropwise while stirring; the reaction mixture is subsequently stirred at reflux temperature for a further 30 minutes and then allowed to cool to room temperature, 50 ml of water are added, the pH of the mixture is adjusted to 5-6 using dilute hydrochloric acid, and the organic phase is separated off, washed twice with water and dried over sodium sulphate, and the solvent is removed in vacuo. The residue is purified by chromatography on silica gel (eluent: diethyl ether).

10.6 g (24% of theory) of 1-(1-chlorocyclopropyl)-1-(3-pyridyl)- 2-(4-chlorophenoxy)-ethanol are obtained as an oil with a refractive index $n_D^{20}=1.5665$.

Example II-2

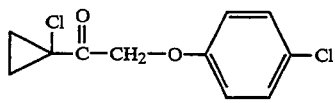

50.4 g (0.392 mol) of 4-chlorophenol and 54.1 g (0.392 mol) of potassium carbonate are heated in 400 ml of toluene at reflux temperature on a water separator for 2 hours while stirring. Subsequently, 50.0 g (0.327 mol) of 1-chlorocyclopropyl-2-chloro-ethan-1-one (cf. e.g. EP 297 383) are added at 100° C., and the mixture is stirred at 100° C. for a further 6 hours. For the working up, the cooled reaction mixture is added to water, and the organic phase is separated off, washed twice with 200 ml of 10 per cent sodium hydroxide solution on each occasion and subsequently washed with water, dried over sodium sulphate and concentrated in vacuo.

66.0 g (82% of theory) of 1-chlorocyclopropyl-2-(4-chlorophenoxy)-ethan-1-one are obtained with a melting point of 78° C.

In a corresponding manner, and according to the general instructions for the preparation, the following substituted hydroxyalkylpyridines of the formula (I) are obtained:

(I)

| Ex. No. | X | A | Ar | physical properties |
|---|---|---|---|---|
| 3 | Cl | O | 2,3-dichlorophenyl | $^1$H-NMR*): 4.37; 4.4; 4.71; 4.74 (q, 2H) |
| 4 | F | O | 2-methyl-4-chlorophenyl | $^1$H-NMR*) 2.04(3H) |
| 5 | F | O | 2,4-dichlorophenyl | $^1$H-NMR*): 3.65(1H) |
| 6 | Cl | O | 4-methylphenyl | $^1$H-NMR*): 2.28(3H) |
| 7 | Cl | S | 4-methylphenyl | $^1$H-NMR*): 2.31(3H) |
| 8 | Cl | O | 2,4-dimethyl-3-chlorophenyl | $^1$H-NMR*): 2.21(3H); 2.24(3H) |
| 9 | Cl | O | 3,4-dimethylphenyl | $^1$H-NMR*): 2.21(3H); |
| 10 | Cl | O | 3-methyl-4-chlorophenyl | $^1$H-NMR*): 2.21(3H); 2.24(3H) |
| 11 | Cl | S | 4-chlorophenyl | $^1$H-NMR*): 3.69; 3.37; 3.96; 4.01(q, 2H) |
| 12 | Cl | S | phenyl | $^1$H-NMR*): 3.73; 3.77; 3.99; 4.04(q, 2H) |

-continued

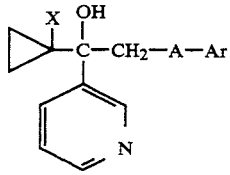
(I)

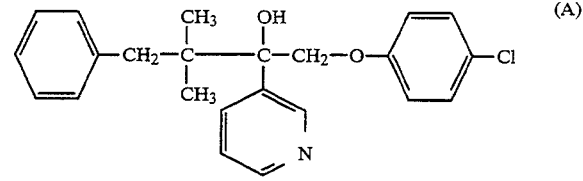
(A)

| Ex. No. | X | A | Ar | physical properties |
|---|---|---|---|---|
| 13 | Cl | O | 4-Cl, 3-CH3 phenyl | ¹H-NMR*): 2.40(3H); |
| 14 | Cl | O | 4-OCH3 phenyl | ¹H-NMR*): 2.69; 3.71(3H); |
| 15 | Cl | O | 4-C(CH3)3 phenyl | ¹H-NMR*): 4.39; 4.43; 4.7; 4.74 (q, 2H); 1.30(9H) |
| 16 | Cl | O | 4-Br phenyl | ¹H-NMR*): 4.37; 4.4; 4.69; 4.72 (q, 2H) |
| 17 | Cl | O | 2,4-di-CH3 phenyl | ¹H-NMR*): 2.02(3H); |
| 18 | Cl | O | 4-SCF3 phenyl | ¹H-NMR*): 4.4; 4.43; 4.76; 4.79 (q, 2H); |
| 19 | Cl | O | 2-CH3, 4-Cl phenyl | ¹H-NMR*): 2.04(3H) |
| 20 | Cl | O | 2-Cl phenyl | ¹H-NMR*): 4.61(2H); |

*)The ¹H-NMR spectra were recorded in deuterochloroform (CDCl₃) using tetramethylsilane (TMS) as internal standard. The chemical shift is given as the δ value in ppm.

APPLICATION EXAMPLES

In the following application examples, the compound illustrated below was employed as the substance for comparison:

Example A

Erysiphe Test (Barley)/protective

Solvent: 100 parts by weight of dimethylformamide
Emulsifier: 0.25 part by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

At a concentration of active compound of 250 ppm in the spray liquor, the compounds according to Preparation Examples 1, 2, 6, 10, 11, 18, 19 and 20 show a degree of activity of 100% whereas the degree of activity for the comparison substance (A) is 50%.

Example B

Leptosphaeria Nodorum Test (Wheat)/protective

Solvent: 100 parts by weight of dimethylformamide
Emulsifier: 0.25 part by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a spore suspension of Leptosphaeria nodorum. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

At a concentration of active compound of 100 ppm in the spray liquor the compounds according to Preparation Examples 2 and 6 show a degree of activity of 100% whereas the degree of activity for the comparison substance (A) is 75%.

Example C

Uncinula Test (Vine)/protective

Solvent: 4.7 parts by weight of acetone

Emulsifier: 0.3 part by weight of alkyl-aryl polyglycol ether

To produce a suitable preparation of active compound, one part by weight of active compound is mixed with the stated amounts of solvent and emulsifier, and the concentrate is diluted with water to the desired concentration.

To test for protective activity, young plants are sprayed with the preparation of active substance until dripping wet. After the spray-coating has dried on, the plants are dusted with conidia of the fungus Uncinula necator.

The plants are then placed in a greenhouse at 23° C. to 24° C. and at a relative atmospheric humidity of about 75%.

Evaluation is effected 14 days after the inoculation.

At a concentration of active compound of 25 ppm in the spray liquor the compounds according to Preparation Examples 1, 2, 3, 6, 14, 15, 16, 17, 18, and 19 show a degree of activity of at least 96%.

What is claimed is:

1. A substituted hydroxyalkylpyridine of the formula

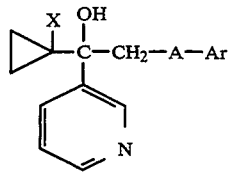

in which
X represents halogen,
A represents oxygen or sulphur and
Ar represents optionally substituted aryl,
or an addition product thereof with an acid or metal salt.

2. A substituted hydroxyalkylpyridine according to claim 1, in which
X represents fluorine, chlorine, bromine or iodine,
A represents oxygen or sulphur and
Ar represents aryl having 6 to 10 carbon atoms, which is optionally substituted identically or differently once or more than once, with suitable substituents selected from the group consisting of:
halogen, cyano, nitro, in each case straight-chain or branched alkyl, alkoxy, alkylthio, alkylsulphinyl or alkylsulphonyl having in each case 1 to 4 carbon atoms, in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, in each case straight-chain or branched alkoxycarbonyl or alkoxyiminoalkyl having in each case 1 to 4 carbon atoms in the individual alkyl moieties, cycloalkyl having 3 to 8 carbon atoms as well as phenyl, which is optionally substituted identically or differently once to more than once by halogen, straight-chain or branched alkyl, straight-chain or branched alkoxy, straight-chain or branched halogenoalkyl and/or straight-chain or branched halogenoalkoxy having in each case 1 to 4 carbon atoms and optionally 1 to 9 identical or different halogen atoms.

3. A substituted hydroxyalkylpyridine according to claim 1, in which
X represents fluorine, chlorine or bromine,
A represents oxygen or sulphur and
Ar represents aryl having 6 or 10 carbon atoms, which is optionally substituted identically or differently once to five times, with suitable substituents selected from the group consisting of:
halogen, cyano, nitro, in each case straight-chain or branched alkyl, alkoxy, alkylthio, alkylsulphinyl or alkylsulphonyl having in each case 1 to 3 carbon atoms, in each case straight-chain or branched halogenoalkyl, halogenoalkoxy, halogenoalkylthio, halogenoalkylsulphinyl or halogenoalkylsulphonyl having in each case 1 to 3 carbon atoms and 1 to 7 identical or different halogen atoms, in each case straight-chain or branched alkoxycarbonyl or alkoxyiminoalkyl having in each case 1 to 3 carbon atoms in the individual alkyl moieties, cycloalkyl having 3 to 7 carbon atoms as well as phenyl, which is optionally substituted identically or differently once to five times by halogen, straight-chain or branched alkyl, straight-chain or branched alkoxy, straight-chain or branched halogenoalkyl and/or straight-chain or branched halogenoalkoxy having in each case 1 to 3 carbon atoms and optionally 1 to 7 identical or different halogen atoms.

4. A substituted hydroxyalkylpyridine according to claim 1, in which
X represents fluorine or chlorine,
A represents oxygen or sulphur and
Ar represents phenyl, which is optionally substituted identically or differently once to five times, with suitable substituents selected from the group consisting of:
fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, methylsulphinyl, ethylsulphinyl, methylsulphonyl, ethylsulphonyl, trifluoromethyl, difluoromethyl, trifluoromethoxy, difluoromethoxy, trifluoromethylthio, trifluoromethylsulphinyl, trifluoromethylsulphonyl, methoxycarbonyl, ethoxycarbonyl, methoxyiminomethyl, methoxyiminoethyl, ethoxyiminomethyl, ethoxyiminoethyl, cyclopropyl, cyclopentyl, cyclohexyl or phenyl, which is optionally substituted identically or differently once to three times by fluorine, chlorine, bromine, methyl, ethyl, n- or i-propyl, methoxy, ethoxy, trifluoromethyl or trifluoromethoxy.

5. A compound according to claim 1, wherein such compound is 1-(1-chlorocyclopropyl)-1-(3-pyridyl)-2-(4-chlorophenoxy)-ethanol of the formula

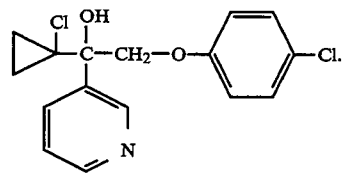

6. A compound according to claim 1, wherein such compound is 1-(1-chlorocyclopropyl)-1-(3-pyridyl)-2-(2-chlorophenoxy)-ethanol of the formula

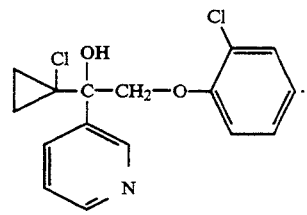

7. A compound according to claim 1, wherein such compound is 1-(1-chlorocyclopropyl) -1-(3-pyridyl)-2-(4-methylphenoxy)-ethanol of the formula

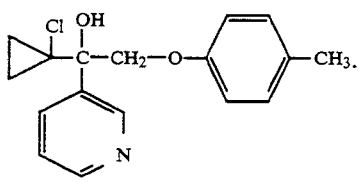

8. A compound according to claim 1, wherein such compound is 1-(1-chlorocyclopropyl)-1-(3-pyridyl)-2-(2,4-dichlorophenoxy)-ethanol of the formula

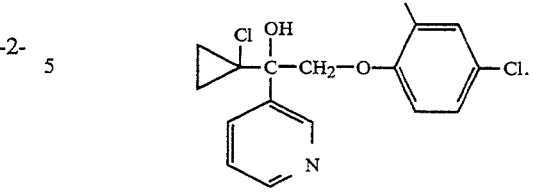

9. A compound according to claim 1, wherein such compound is 1-(1-chlorocyclopropyl)-1-(3-pyridyl)-2-(2-methyl-4-chlorophenoxy) -ethanol of the formula

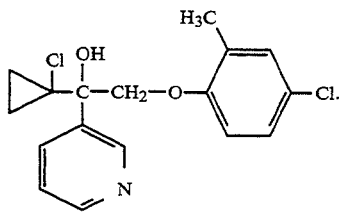

10. A pesticidal composition comprising a pesticidally effective amount of a compound or addition product according to claim 1 and an inert diluent.

11. A method of combating pests, which method comprises applying to such pests or to their habitat a pesticidally effective amount of a compound or addition product according to claim 1.

12. A method according to claim 11, wherein such compound is
1-(1-chlorocyclopropyl)-1-(3-pyridyl)-2-(4-chlorophenoxy)-ethanol or
1-(1-chlorocyclopropyl)-1-(3-pyridyl)-2-(2-chlorophenoxy)-ethanol or
1-(1-chlorocyclopropyl)-1-(3-pyridyl)-2-(4-methylphenoxy)-ethanol or
1-(1-chlorocyclopropyl)-1-(3-pyridyl)-2-(2,4-dichlorophenoxy)-ethanol or
1-(1-chlorocyclopropyl)-1-(3-pyridyl)-2-(2-methyl-4-chlorophenoxy)-ethanol.

* * * * *